United States Patent [19]
Piasek et al.

[11] 3,985,802
[45] Oct. 12, 1976

[54] LUBRICATING OILS CONTAINING HIGH MOLECULAR WEIGHT MANNICH CONDENSATION PRODUCTS

[75] Inventors: Edmund J. Piasek, Chicago, Ill.; Robert E. Karll, Munster, Ind.

[73] Assignee: Standard Oil Company (Indiana), Chicago, Ill.

[22] Filed: Oct. 8, 1974

[21] Appl. No.: 513,108

Related U.S. Application Data

[60] Division of Ser. No. 284,222, Aug. 28, 1972, abandoned, which is a division of Ser. No. 798,102, Feb. 10, 1969, Pat. No. 3,798,165, which is a continuation-in-part of Ser. No. 502,368, Oct. 22, 1965, Pat. No. 3,539,633.

[52] U.S. Cl. .......... 260/553 A; 260/552 R; 260/553 R; 260/570.5 P; 260/462 R; 252/47.5; 252/51.5 R
[51] Int. Cl.² ............... C07C 127/17; C07C 157/07
[58] Field of Search ...... 260/553 R, 553 CD, 553.4, 260/553.4 C; 252/51.5 R

[56] References Cited
UNITED STATES PATENTS

| | | | |
|---|---|---|---|
| 1,963,762 | 6/1934 | Pungs et al. | 260/553 R X |
| 2,353,192 | 7/1944 | Sargent et al. | 260/570.5 PA X |
| 2,353,491 | 7/1944 | Oberright | 252/427 X |
| 2,363,134 | 11/1944 | McCleary | 260/570.9 X |
| 2,403,453 | 7/1946 | Otto | 252/51.5 R |
| 3,036,003 | 5/1962 | Verdol | 252/33.4 |
| 3,368,972 | 2/1968 | Otto | 252/47.5 |
| 3,449,362 | 6/1969 | Lee | 260/553 R X |
| 3,725,277 | 4/1973 | Worrel | 252/51.5 R |
| 3,726,882 | 4/1973 | Traise et al. | 252/51.5 R X |
| 3,736,357 | 5/1973 | Piasek et al. | 252/51.5 R X |
| 3,787,458 | 1/1974 | Piasek et al. | 252/51.5 R X |
| 3,787,492 | 1/1974 | Lee | 260/553 R |
| 3,798,247 | 3/1974 | Piasek et al. | 252/51.5 R X |
| 3,859,351 | 1/1975 | Keller et al. | 260/553 R X |
| 3,872,019 | 3/1975 | Culbertson et al. | 252/51.5 R X |

*Primary Examiner*—Robert V. Hines
*Assistant Examiner*—Thomas A. Waltz
*Attorney, Agent, or Firm*—Fred R. Ahlers; Arthur G. Gilkes; William T. McClain

[57] ABSTRACT

Oil soluble high molecular weight Mannich condensation products formed by reacting (1) high molecular weight alkyl-substituted hydroxy aromatic compounds whose alkyl-substituent has a number average molecular weight ($\overline{Mn}$) from about 600-100,000, (2) a compound containing at least one HN< group, and (3) an aldehyde in the respective molar reactant ratio of 1:0.1-10:1.0-10, are highly efficient ashless type (metal free) dispersant-detergent lubricant oil addition agents. Lubricating oils containing these compositions provide a high degree of protection against the deposition of sludge and varnish and corrosion when used as crankcase lubricants. Bis-Mannich products prepared by condensing (1) a 850-2500 $\overline{Mn}$ polyalkyl-substituted phenol, (2) an alkylene polyamine and (3) formaldehyde in the respective molar ratio of 1.0:0.7-1.0:1.5-2.1 are novel products and are especially effective for high severity detergent-dispersant function over the extended oil drain range of crankcase lubricant oils recommended by automobile manufacturers.

3 Claims, No Drawings

LUBRICATING OILS CONTAINING HIGH MOLECULAR WEIGHT MANNICH CONDENSATION PRODUCTS

RELATED APPLICATIONS

This is a division, of application Ser. No. 284,222, filed Aug. 28, 1972, now abandoned, which is a division of application Ser. No. 798,102 filed Feb. 10, 1969, now U.S. Pat. No. 3,798,165, which is a continuation-in-part of our copending application Ser. No. 502,368, filed Oct. 22, 1965 now U.S. Pat. No. 3,539,633.

BACKGROUND OF THE INVENTION

This invention relates to improved lubricating oils and particularly concerns automobile and Diesel crank-case lubricating oil formulations containing a minor amount of a new class of oil-soluble addition agents which improve the performance of the oil, particularly its dispersant-detergent function thus enabling lubricating oils to provide a high degree of protection of the lubricated parts of internal combustion engines.

Present-day automobile and Diesel engines have been designed for higher power output, lower combustion products emission and longer in-service periods of use of crankcase lubricating oils. These design changes have resulted in such severe operating conditions as to necessitate devising higher efficiency lubricating oils that will, under the increased severity of in-service use, afford proper protection against corrosion and the accumulation or deposition of sludge, varnish and resinous materials on the surface of engine parts which rapidly accelerate decrease in both operating efficiency and life of the engine. The principal ingredient of crankcase lubricants is a base lubricating oil, a mixture of hydrocarbons derived from petroleum. Even when highly refined by removal of deleterious components, such as polymerizable components, acid formers, waxes, etc., a lubricant base oil still requires the addition of a number of oil-soluble chemical additives to enable the oil to resist oxidation, deposition of sludge and varnish on, and corrosion of, the lubricated metal parts, and to provide added lubricity and regulated viscosity change from low to high temperature. These ingredients are commonly known as anti-oxidants, dispersant-detergents, pour point dispersants, etc.

Combustion products from the burning of fuel and thermal degradation of lubricating oils and addition agents tend to concentrate in the crankcase oil with the attendant formation of oil-insoluble deposit-forming products, that either surface coat the engine parts (varnish or lacquer-like films) or settle out on the engine parts as viscous (sludge) deposits or form solid ash-like or carbonaceous deposits. Any of such deposits can restrict, and even plug, grooves, channels and holes provided for lubricant flow to the moving surfaces of the engine requiring lubrication thus accelerating the wear and thus reducing the efficiency of the engine. In addition, acidic combustion products corrode the lubricated metal surfaces. Chemical additives are blended in crankcase oil formulations not only to reduce thermal decomposition of the oil and addition agents (anti-oxidants) but also to keep in suspension (as a dispersant) and to resuspend (as a detergent) insoluble combustion and degradation products as well as to neutralize acidic products (anti-corrosion agents). A separate additive is usually added for each improvement to be effected.

Various ingredients have been developed for the purpose of providing the dispersant-detergent function. Neutral and overbased metallo-organic compounds, such as the alkaline earth metal salts of sulfonic acids and hydrocarbon-$P_2S_5$ reaction products were the first addition agents used for this purpose. Their in-service drawbacks included the formation of metal-ash thermal decomposition products which deposited on engine parts; they could not efficiently disperse or resuspend lacquer or varnish formers or sludge formers; and they lost their dispersant-detergent function when their alkaline earth metal component had been consumed in neutralizing acidic products of combustion.

As performance levels increased and the recommended periods between oil drains lengthened for both automobile and railway Diesel engines, more efficient dispersancy and detergency performance as well as acid neutralization and lower ash-forming tendency were demanded for lubricating oil formulations. During the past several years, a great deal of time and effort has been directed at providing addition agents for lubricants capable of satisfying such performance demands. When high molecular weight polybutene polymers became commercially available in the early 1940's, research workers in various laboratories devised, for this dispersant-detergent function, a series of derivatives of polybutene-phosphorus pentasulfide reaction products, e.g., alkaline earth metal salts, alkylene polyamine and alkylene oxide derivatives, in which the high molecular weight of the polybutene group greatly enhanced their effectiveness. Other devised amine salts, amides, imides and amidines of polybutenyl-substituted polycarboxylic acids and polymeric compounds having pendant or grafted-on polar groups. Still other suggested combinations of alkaline earth metal sulfonates and Mannich condensation products of a low molecular weight alkyl ($C_2$–$C_{20}$) substituted hydroxyaromatic compound, an amine having at least one replaceable hydrogen on a nitrogen and an aldehyde and alkaline earth metal salts (phenates) of those Mannich condensation products but without notable success. The latter compositions still possessed the objectionable feature of forming harmful metal-ash deposits, and were incapable of providing the increased dispersancy-detergency service demanded for long drain service of present-day engine requirements.

Mannich condensation products derived from alkyl-substituted hydroxyaromatic compounds having a relatively low molecular weight alkyl substituent, i.e., 2 to 20 carbon atoms in the alkyl substituent and chlorinated wax (straight chain) type alkyl-substituents are described in U.S. Pat. Nos. 2,403,453; 2,353,491; 2,363,124; 3,459,112; 2,984,550 and 3,036,003. However, none of such prior Mannich condensation products are suitable for use as dispersant-detergent addition agents for present-day long drain oil interval in-service use.

One known type (U.S. Pat. No. 2,363,134) has been prepared by reacting, under Mannich reaction conditions, equimolar quantities of a $C_2$–$C_{20}$ alkyl-substituted phenol and other hydroxy aromatic compounds, and N,N-di-substituted amine and formaldehyde according to the following equation:

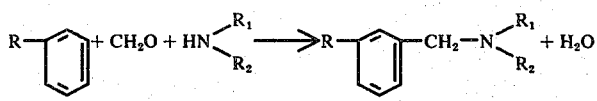

wherein R is an alkyl group having between 2 and 20 carbon atoms and $R_1$ and $R_2$ may be alkyl, cycloalkyl, aryl or arakyl radicals.

Other prior low molecular weight Mannich condensation products formed by condensing a $C_2$ to $C_{20}$ alkyl-substituted phenol, an alkylene diamine and an aldehyde in the respective molar ratios of 2:1:2, have been illustrated by the following structural formula:

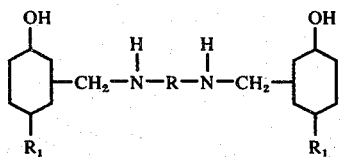

wherein R is a divalent alkylene hydrocarbon radical and $R_1$ is an alkyl group containing from 2 to 20 carbon atoms.

Still others have been prepared by reacting $C_2$–$C_{20}$ alkylphenols, formaldehyde and alkylene polyamines of the formula

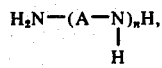

wherein A is a divalent alkylene radical of 2 to 6 carbon atoms and $n$ is an integer from 1 to 10, in the ratio of from 0.5 to 2 moles each of $C_2$–$C_{20}$ alkylphenol and formaldehyde for each nitrogen group contained in the alkylene polyamine reagent. The molar reactant ratio range of $C_2$–$C_{20}$ alkylphenol, amine and formaldehyde used to form such products is 1–20:1.0:1–20. U.S. Pat. No. 3,036,003 exemplifies such products, which usually are formed with ethylene polyamines, according to the above formula in which A is —$CH_2$—$CH_2$— and N is 2, 3 and 4. For example, reaction of p-tertiary octylphenol, diethylene triamine, and formaldehyde in the respective molar ratios of 3:1:3 is illustrated in said patent as $N_1$, $N_2$, $N_3$-tri-(2-hydroxy-5-t-octylbenzyl) di-ethylene triamine and the reaction of the aforesaid reactants in the respective molar ratios of 2:1:2 is illustrated as being either $N_1$, $N_3$ or $N_1$, $N_2$-di-(2-hydroxy-5-t-octylbenzyl) diethylene triamine.

The foregoing prior $C_2$–$C_{20}$ alkyl-substituted Mannich condensation products commonly are prepared by the conventional technique of adding the aliphatic aldehyde to a heated mixture of the alkylhydroxyaromatic and amine reagents, in the presence or absence of a solvent, and then heating the resultant mixture to a temperature between 100°–350° F. until dehydration is complete. A solvent such as benzene, toluene, xylene, methanol and others easily separated from the reaction mixture are light mineral oils, such as those used in blending stocks to prepare lubricating oil formulations in which the product is formed as a mineral oil concentrate are usually used. The water by-product is removed by heating the reaction mixture to a temperature sufficiently high, at least during the last part of the process, to drive off the water alone, or as an azeotropic mixture with the aromatic solvent, usually by the aid of an inert stripping gas, such as nitrogen, carbon dioxide, etc.

The exactly neutralized or overbased alkaline earth metal salts (alkaline earth metal phenates) of those prior low molecular weight Mannich condensation products have been suggested for use in providing lubricating oils with a combination of detergent-inhibitor properties in one addition agent. The exactly neutralized alkaline earth metal salts have one equivalent of alkaline earth metal for each hydroxy group present. The overbased salts have, for each hydroxy group present, more than one equivalent of alkaline earth metal in the form of a hydroxy metaloxy, alkoxy metaloxy and even alkaline earth metal carbonate complex with hydroxy metaloxy on each benzene group as a replacement for the phenol hydroxy group. As noted above, said addition agents form objectionable metal ash deposits and have other performance deficiencies.

Certain hydroxy $C_2$–$C_{20}$ alkylbenzyl substituted ethylene polyamines have been suggested, in U.S. Pat. No. 3,036,003, as being useful per se in lubricating oil formulations of ashless-type detergents. The product resulting from the reaction of p-tertiary-octylphenol, tetraethylene pentamine and formaldehyde in a molar reactant ratio of 4:1:4, characterized as the tetra-(hydroxy-5-tertiary-octylbenzyl) derivative of tetraethylene pentamine is indicated, by said patent, as capable of imparting detergency to lubricating oils on the basis of a carbon black suspension test described in the patent. However, that patent itself demonstrates, by an oxidation stability test, that the very same product is a lubricating oil formulation, with no other detergent added, permits sludge and varnish formation as well as oxidation of the base oil. Thus, U.S. Pat. No. 3,036,003 demonstrates that its Mannich condensation products, when added as the sole detergent agent in a lubricating oil, are incapable of providing a satisfactory level of detergency and are also incapable of inhibiting oxidation of the base oil.

U.S. Pat. No. 3,235,484 issued February 15, 1966 (now Reissue No. 26,330) describes the addition agents of certain disclosed compositions to refinery hydrocarbon feed stocks for the purpose of inhibiting the accumulation of carbonaceous deposits in refinery cracking units. The primary inhibitors disclosed are mixtures of amides, imides and amine salt formed by reacting an ethylene polyamine with hydrocarbon substituted succinic acids or anhydride, whose hydrocarbon substituent has at least about 50 carbon atoms. As an adjunct for such primary carbonaceous depost inhibitors there is disclosed in said patent Mannich condensation products formed by reacting (1) alkylphenol, (2) an amine and (3) formaldehyde in the ratio of one mole alkylphenol and from 0.1–10 mole formaldehyde for each active nitrogen group contained in the amine reactant. Alkylphenols whose alkyl group has a molecular weight as high as 50,000 and contains from monoalkylphenols whose alkyl group contains 4–30 carbon atoms are stated to be the preferred alkylphenol reactants.

BRIEF SUMMARY OF THE INVENTION

This invention pertains to improved lubricating oils and is predicated upon the discovery of a new class of multifunctional addition agents for lubricating oils, particularly those used in internal combustion engines in which they function as highly efficient dispersant-detergent and also act as inhibitors of oxidation.

The new class of compounds which are employed as additives according to our invention are oil-soluble high molecular weight Mannich condensation products. They may be prepared in the usual manner by condensing under Mannich reaction conditions:

1. an alkyl-substituted hydroxyaromatic compound, whose alkylsubstituent has a 600–100,000 $\overline{M}n$, preferably a polyalkylphenol whose polyalkyl substituent is derived from 1-mono-olefin polymers having a $\overline{M}n$ of about 850–2500;

2. an amine containing at least one >NH group, preferably an alkylene polyamide of the formula

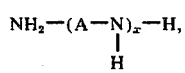

wherein A is a divalent alkylene radical having 2 to 6 carbon atoms and X is an integer from 1 to 10; and 3. an aldehyde, preferably formaldehyde.

In general, the foregoing high molecular weight Mannich condensation products of this invention are prepared according to the conventional methods heretofore employed for the preparation of low molecular weight Mannich condensation products, using the above-named reactants in the respective molar ratios of high molecular weight alkyl-substituted hydroxyaromatic compound, amine and aldehyde of approximately 1:0.1–10:1.0–10. They may conveniently be prepared by the usual Mannich condensation procedure which involves adding the formaldehyde reagent (e.g., formalin) to a mixture of reagents (1) and (2) above or in an easily removed organic solvent, such as benzene, xylene or toluene or in solvent refined neutral oil and then heating the reaction at an elevated temperature (100–350° F.) until dehydration is complete.

The preferred additives according to this invention are high molecular weight bis-Mannich condensation products formed by reacting (1) a 850–2500 $\overline{M}n$ polyalkylphenol; (2) an ethylene polyamine, bis-carbamide or bis-thiocarbamide as amine reactant; and (3) formaldehyde in the respective molar ratio of 1.0:0.7–1.0:1.5–2.1. These can be prepared by the general method or by a two-step condensation method in which the formaldehyde is added in two reaction stages in lieu of adding all of the formaldehyde to reactants (1) and (2) as in the general procedure. For example, when the two-step precedure is employed using a respective reactant molar ratio of 1.0:0.7:1.5, all of the alkylphenol and amine reactant and about two-thirds of the formaldehyde are heated, usually in a solvent such as mineral oil, at approximately 130°–300° F. until dehydration is complete to form an intermediate Mannich condensation product. Thereafter the remaining portion of formaldehyde is added, usually at 150°–300° F., and the resulting mixture heated and maintained at approximately 250°–350° F. from 1 to 5 hours until dehydration is complete to form the final product.

With equimolar amounts of all reactants, the theoretical first-stage intermediate product is 1:1:1 condensation product. Infrared analysis of this intermediate product indicates, by the strong 12.1 micron band representing the unsubstituted 5 and 6 ring positions, the presence of a single —$CH_2$ group on the benzene ring in the position ortho to the hydroxy group substituent. On the basis of infrared data, the predominant first-step product formed using a high molecular weight alkylphenol, formaldehyde and an alkylene polyamine, bis-carbamide or bis-thiocarbamide, may be postulated as having the following structure:

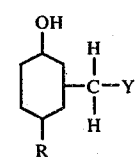

wherein R is an alkyl radical containing from 50 to 20,000 carbon atoms and Y is

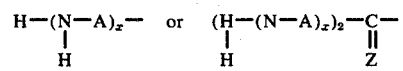

wherein A is a saturated alkylene radical having from 2 to 6 carbon atoms, X is an integer from 1 to 10 and Z is oxygen or sulfur. The latter are prepared from bis-carbamides and bis-thiocarbamides of polyalkylene polyamines by reacting 2 moles of polyalkylene polyamine with 1 mole of urea or thiourea, respectively, accompanied by liberation of 2 moles of ammonia.

The second-stage product formed by reaction of the first-step intermediate with an additional mole of formaldehyde also exhibits a strong 12.1 micron infrared band. This would tend to exclude the formation of products having a methylene bridge linking 2 moles of the first-step intermediate to 5 and/or 6 ring position carbons in each mole. It appears probable that the formaldehyde used in the second step reacts with at least one of the terminal primary amino groups to form a —NH—$CH_2OH$ terminal group as an intermediate which can thus react with a hydrogen of other terminal primary amino group or with the hydrogen on a 6 position carbon (the OH group retains its ortho directing character). In either type of condensation, water is formed as a by-product. When the second formaldehyde reaction step involves a condensation of the formaldehyde and hydrogen of both terminal primary amino groups, such a product can be called a "tail-to-tail" product. When the formaldehyde of the second reaction step reacts with one hydrogen of one terminal primary amino group to provide an N-(hydroxy methyl) substituent which, in turn, reacts with a 6 hydrogen splitting out water as a byproduct, the final product can be called a "tail-to-head" product.

On this basis, the foregoing bis-Mannich reaction products may be postulated as containing compounds having the following structural formulas:

Tail-to-Tail

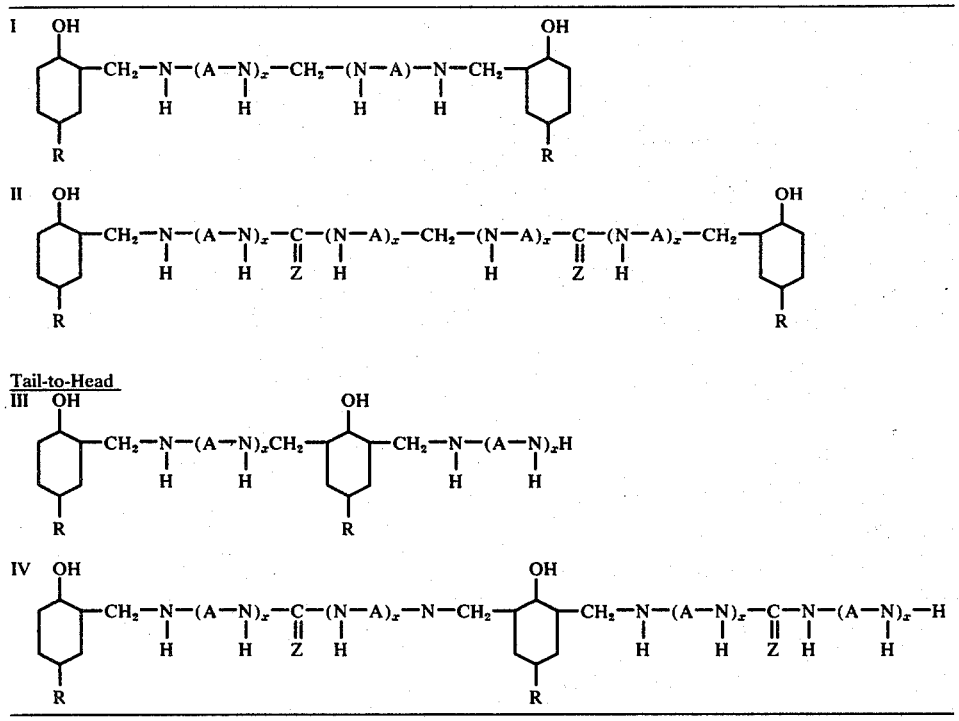

wherein A, x and Z are as hereinbefore defined.

The above-described two-step process and general Mannich condensation preparative technique of adding all of the aldehyde reagent to a mixture of the high molecular weight hydroxyaromatic compound and an alkylene polyamine or bis-carbamide and then heating the mixture until dehydration is complete, produced, from the respective molar ratios of these reactants of 1:0.7–1:1.5–2.1 products substantially equivalent in nitrogen utilization, viscosity and in-service performance as dispersant-detergent addition agents.

The novel addition agents according to our invention are the high molecular weight Mannich condensation products of (1) high molecular weight alkyl substituted phenol whose alkyl substituent has a Mn of 600 – 100,000, a compound having at least one HN< group and an aldehyde wherein the respective molar ratio of the reactants is 1:0.1–10:1.0–10. Preferred addition agents are those obtained by condensing (1) an alkylphenol whose alkyl substituent is derived from 1-mono-olefin polymers having a 850 – 2500 Mn; (2) an alkylene polyamine having the formula $H_2N\text{-}(A\text{-}NH)_nH$ or a bis-(polyaminoalkyl) urea having the formula

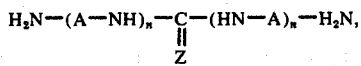

wherein A is a divalent saturated hydrocarbon radical having 2 to 6 carbon atoms and n is an integer from 1 to 10, and (3) a formaldehyde yielding reactant used in the respective molar ratio of reactants is 1:0.7–10:1-.5–2.1.

The high molecular weight Mannich condensation products of this invention are exceptionally useful addition agents for lubricating oils imparting thereto dispersant-detergent and anti-oxidant properties at relatively low concentrations of the addition agent, e.g., 0.05 to 10 weight percent in formulated crankcase lubricating oil. Higher concentrations, e.g., 10 to 70 weight percent, are useful concentrates of the preparation of those formulated crankcase lubricating oils and the fortification of crankcase oil in use prior to the scheduled complete drain. In contrast, Mannich condensation products formed using low molecular weight alkyl substituted hydroxyaromatic compounds whose alkyl group contains 2 to 20 carbon atoms are unacceptable as dispersant-detergent addition agents for crankcase lubricating oils.

The foregoing superiority of the high molecular weight Mannich condensation products of this invention over the low molecular weight Mannich condensation products of the prior art is amply demonstrated by a comparison of their respective abilities to prevent sludge and varnish deposition in standardized industry accepted engine tests. One of the prerequisites for acceptance as a dispersant-detergent agent for in-service use in lubricating oils for present-day engines is the ability of an addition agent to effectively provide, in those tests, a lubricating oil having a highly efficient dispersancy-detergency function, which function is rated at the end of the engine tests, by visual inspection of the disassembled engine parts for sludge and varnish deposits. The results of the tests are scored on a 0–50 scale, a reading of 50 representing a clean engine free from detectable sludge and varnish. To be acceptable as a dispersant-detergent addition agent, a candidate must score on overall sludge and varnish deposit rating of 40 and over.

Low molecular weight $C_2$–$C_{20}$ alkyl-substituted Mannich condensation products when used in crankcase lubricating oils as the sole source of dispersant-detergent addition agent at maximum concentration levels at which they can be incorporated in lubricating oil are unable to provide acceptable sludge or varnish ratings when evaluated in such standardized engine tests. On the other hand, the high molecular weight Mannich condensation products of this invention used as the sole dispersant-detergent addition agents in lubricating oils in the range of 0.05–10, preferably 0.5–5.0, weight percent, provide crankcase lubricating oils which, when evaluated by the same standardized engine tests, scored sludge and varnish ratings of 40 and higher, even as high as 45 to 49.5.

EMBODIMENTS OF THE INVENTION

Representative high molecular weight Mannich condensation products contemplated by this invention can be prepared by the following representative reactants of the classes before defined.

1. High Molecular Weight Alkyl-Substituted Hydroxyaromatics

Representative of these high molecular weight alkyl-substituted hydroxyaromatic compounds are polypropylphenol, polybutylphenol and other polyalkyl phenols. These polyalkylphenols may be obtained by the alkylation, in the presence of an alkylating catalyst, such as $BF_3$, of phenol with high molecular weight polypropylene, polybutylene and other polyalkylene compounds to give alkyl substituents on the benzene ring of phenol having an average 600 – 100,000 $\overline{M}n$. Their preparations using a $BF_3$ phenol catalyst is described and claimed in our copending application Serial No. 484,758, filed September 2, 1965.

The 600 $\overline{M}n$ and higher $\overline{M}n$ alkyl-substituents on the hydroxyaromatic compounds may be derived from high molecular weight polypropylenes, polybutenes and other polymers of mono-olefins, principally 1-mono-olefins. Also useful are copolymers of mono-olefins with monomers copolymerizable therewith wherein the copolymer molecule contains at least 90%, by weight, of mono-olefin units. Specific examples are copolymers of butenes (butene-1, butene-2 and isobutylene) with monomers copolymerizable therewith wherein the copolymer molecule contains at least 90%, by weight, of propylene and butene units, respectively. Said monomers copolymerizable with propylene or said butenes include monomers containing a small proportion of unreactive polar groups such as chloro, bromo, keto, ethereal, aldehyde, which do appreciably lower the oil-solubility of the polymer. The comonomers polymerized with propylene or said butenes may be aliphatic and can also contain non-aliphatic groups, e.g., styrene, methyl styrene, p-dimethyl styrene, divinyl benzene and the like. From the foregoing limitation placed on the monomer copolymerized with propylene or said butenes, it is abundantly clear that said polymers and copolymers of propylene and said butenes are substantially aliphatic hydrocarbon polymers. Thus the resulting alkylated phenols contain substantially alkyl hydrocarbon substituents having $\overline{M}n$ upward from 600.

In addition to these high molecular weight hydroxyaromatic compounds others which may be used include those which have been used to prepare prior low molecular weight Mannich condensation products, e.g., high molecular weight alkyl-substituted derivatives of resorcinol, hydroquinone, cresol, catechol, xylenol, hydroxy diphenyl, benzylphenol, phenethylphenol, naphthol, tolylnaphthol, among others. Preferred for the preparation of the before mentioned preferred bis Mannich condensation products are the polyalkylphenol reactants, e.g., polypropylphenol and polybutylphenol whose alkyl group has an average number molecular weight of 600 – 3000, the most preferred being polybutylphenol whose alkyl group has an average number molecular weight of 850 – 2500.

2. HN< Group Containing Reactants

Representative of this class of reactants are alkylene polyamines, principally polyethylene polyamines. Other representative organic compounds containing at least one HN< group suitable for use in the preparation of Mannich condensation products are well known and include the mono and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Suitable alkylene polyamine reactants include ethylendiamine, diethylene triamine, triethylene tetramine, tetraethylene pentamine, pentaethylene hexamine, hexaethylene hapta-amine, heptaethylene octamine, octaethylene nonamine, nonaethylene decamine and decaethylene undecamine and mixture of such amines having nitrogen contents corresponding to the alkylene polyamines, in the formula $H_2N-(A-N-H-)_nH$, mentioned before, A is divalent ethylene and $n$ is 1 to 10 of the foregoing formula. Corresponding propylene polyamines such as propylene diamine and di-, tri- tetra-, penta-propylene tri-, tetra-, penta- and hexa-amines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloro alkanes having 2 to 6 carbon atoms and the chlorines on different carbons are suitable alkylene polyamine reactants.

Also suitable are condensation products of urea or thiourea and the alkylene polyamines wherein for each X moles of urea or thiourea 2X moles of alkylene polyamine are used. Such a condensation product from two moles of alkylene polyamine and one mole of urea has the formula:

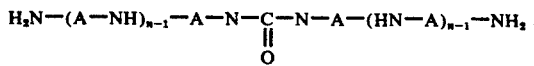

Aldehyde Reactants

Representative aldehyde reactants contemplated for use in the preparation of the high molecular weight Mannich condensation products of this invention include the aliphatic aldehydes such as formaldehyde (also as paraformaldehyde and formalin), acetaldehyde and aldol (b-hydroxybutyraldehyde). We prefer to use formaldehyde or a formaldehyde yielding reactants.

The following examples will serve to illustrate specific embodiments of this invention prepared according to the well-known classical one-step Mannich condensation process.

EXAMPLE 1

There are combined, stirred and heated to 320° F., 50 grams of SAE 5W weight oil, 100 grams (0.112 mole) of 892 $\overline{M}n$ polypropyl ($C_{57}$) substituted phenol and 5.24 ml. (0.0283 mole) tetraethylene pentamine. Thereafter 0.122 mole formaldehyde is added rapidly.

Nitrogen is injected into the stirred mixture held at 300° F. for 90 minutes to remove by-product water. The dried solution is clear and has a red color. The solution contains 68.8% of high molecular weight (985 $\overline{Mn}$) Mannich condensation product of 1.8% nitrogen. The respective molar ratio of reactants substituted phenol:amine:aldehyde used is 1:0.25:1.09.

To demonstrate the dispersancy property of the high molecular weight Mannich condensation product of Example 1, there is dissolved 0.264 gram of the solution in 90 ml. of naphtha. To that naphtha solution there is added 4.0 grams of lamp black, the mixture is shaken and permitted to stand overnight (about 16 hours). After standing 16 hours the carbon black was still well dispersed in the naphtha solution of the solution of high molecular weight Mannich condensation product prepared according to Example 1.

EXAMPLE 2

There are combined, stirred and heated to 200° F., 200 grams (0.222 mole) of polypropyl ($C_{57}$) phenol of 900 $\overline{Mn}$ and 10.5 ml. (0.055 mole) tetraethylene pentamine. Thereafter 0.25 mole formaldehyde (20 ml. of formalin) is added all at one time. The mixture became frothy and viscous. After frothing subsided (upon cooling) the mixture is heated and injected with nitrogen until the product is substantially free of by-product water. This high molecular weight Mannich condensation product has a viscosity at 210° F. of 21,621 SSU, is soluble in lubricating oil and has a 2300 $\overline{Mn}$. The ratio of polypropylphenol:amine:aldehyde reactants used is in the molar ratio of 1:0.247:1.126.

EXAMPLE 3

The method of Example 2 is repeated except 0.055 mole diethylene triamine is used in place of 0.055 mole tetraethylene pentamine. The resulting product is all high molecular weight (2023 $\overline{Mn}$) Mannich condensation product, soluble in lubricating oil and has a viscosity of 16,340 SSU at 210° F. The ratio of polypropylphenol:amine:aldehyde reactants used is in the molar ratio of 1:0.247:1.126. The product of this method is a clear liquid at 210° F.

EXAMPLE 4

There are combined, stirred and heated to 180° F. a mixture of 200 grams (0.222 mole) of 900 $\overline{Mn}$ polypropyl substituted phenol and 84 grams (0.444 mole) of tetraethylene pentamine. Thereafter 36 ml. of formalin solution (37% $CH_2O$) to provide 0.444 mole of formaldehyde is added rapidly. The temperature of the reaction mixture increases during formalin addition. After adding formalin the stirred mixture is heated to 300° F. and held there for several hours and then held at reduced pressure under vacuum distillation conditions to remove by-product water. The dried product is all high molecular weight (994 $\overline{Mn}$) Mannich condensation product having a viscosity of 3386 SSU at 210° F. The ratio of phenol:amine:aldehyde used is in the molar ratio of 1:2:2.

EXAMPLE 5

The preparative method of Example 4 is repeated using the same reactants except in the quantities of 0.222 mole of 900 $\overline{Mn}$ polypropyl substituted phenol, 0.111 moletetraethylene pentamine and 0.222 mole of formaldehyde to provide the respective molar ratio of 1:0.5:1. The resulting product is all high molecular weight Mannich condensation product (1892 $\overline{Mn}$) having a viscosity of 13,840 SSU at 210° F.

EXAMPLE 6

There are combined, stirred and heated to 180° F., 0.222 mole of polypropyl substituted phenol (900 $\overline{Mn}$) and 0.222 mole of diethanolamine. Thereafter 0.222 mole of formaldehyde is added and then the temperature of the stirred mixture is raised to 310° F. At that temperature nitrogen was injected into the stirred liquid to remove by-product water. The respective molar ratio of phenol:amine:aldehyde used is 1:1:1. The dried liquid product is clear but upon cooling becomes a dark viscous liquid and has a molecular weight (1005 $\overline{Mn}$) and a viscosity of 16,269 SSU at 210° F.

To 90 ml. of naphtha there is added 0.1 gram of the product of Example 6 and 4 grams of lamp black in 16 grams of white oil. This mixture is shaken and permitted to stand 20 hours. After standing 20 hours the carbon black was still well dispersed.

EXAMPLE 7

There are combined, stirred and heated to 200° F. 0.445 mole of polypropyl-substituted phenol (900 $\overline{Mn}$) and 0.111 mole tetraethylene pentamine. Then 36 ml. formalin (37% $CH_2O$) is added to provide 0.445 mole formaldehyde. This mixture is quite viscous at 200° F. so to facilitate stirring the reaction product is heated to 300° F. and injected with nitrogen to remove by-product water. The dried product is all high molecular weight (3800 $\overline{Mn}$) Mannich condensation product. The ratio of phenol:amine:aldehyde used is the respective molar ratio of 1:0.249:1.

It is desirable to know the anti-corrosion protection to bearing metals afforded by detergent-dispersants. One test used is the Stirred Sand Corrosion Test. This Test is conducted in an iron beaker to which are added 250 grams of solvent extracted SAE 30 weight oil, a tared copper-lead bearing, suspended in the oil, 50 grams of 30–35 mesh (Tyler Screen Size Standard) sand, 0.625 grams lead oxide, 1.25 grams of a zinc dialkyl dithiophosphate oxidation inhibitor, and the detergent-dispersant detergent. The Cu-Pb bearing is lightly abraded with steel wool, washed with naphtha, dried and weighed to the nearest milligram before suspending it in the oil. The beaker and its contents are kept at a constant temperature of 300° F. (±2° F) while the contents are stirred at 750 RPM in contact with air. Lead oxide is used to simulate blow-by of lead past piston rings from combustion of leaded fuels into the engine crankcase. At the end of the test the bearing is removed, washed with naphtha, dried and weighed to the nearest milligram. Acidity of the oil after the test is determined in milligrams KOH per gram sample of oil. Tests are run on duplicates, one for 48 hours and one for 72 hours. The results of these tests conducted with high molecular weight Mannich condensation products of this invention and a control bis-succinimide detergent-dispersant are set out in the following table.

| STIRRED SAND CORROSION TEST RESULTS | | | | | |
|---|---|---|---|---|---|
| Detergent-Dispersant | | Bearing Weight Loss-mg | | Acidity-mg KOH/gram | |
| Example | Amount | 48 hours | 72 hours | 48 hours | 72 hours |
| 2 | 5 gms | 46.6 | 213.5 | 1.68 | 9.5 |
| 3 | 5 gms | 42.1 | 226.9 | 1.68 | 8.6 |
| 4 | 5 gms | 23.8 | 52.1 | 1.68 | 3.64 |
| 5 | 5 gms | 58.2 | 91.8 | 1.12 | 2.8 |
| 6 | 5 gms | 39.4 | 46.0 | 1.68 | 8.7 |
| Control | 5 gms | 283.9 | 844.8 | 9.0 | 17.4 |
| 7 | 5 gms | 20.8 | 65.9 | 2.24 | N.D. |

In the above table "N.D." indicates no determination for the test in question. The high molecular weight Mannich condensation products do, as the tabulated test data indicate, exert anti-corrosion properties to lubricating oil.

A bench test (Stirred Oxidation Test) for pre-evaluation of inhibition of sludge (naphtha insolubles) varnish and acidity formation by dispersant-detergent additive consists of dissolving 6 grams of the additive in 300 grams of solvent extracted SAE 30 weight oil in a beaker, suspending in the oil 5 square inches of copper and 10 square inches of iron as oxidation catalysts, maintaining the beaker and its contents at 330° F. (±2° F.) while stirring with glass stirie the beaker's contents in contact with air at 1300 RPM. Four glass varnish rods (6 mm diameter) are inserted in the stirred oil. The varnish on the rods is evaluated on a scale of 0 to 10 where 10 is a clean rod. The naphtha insolubles (sludge) is measured as reported as weight percent and acidity is expressed in milligrams KOH per gram of sample. These values are determined at 24, 48 and 72 hour test durations. For such tests using high molecular weight Mannich condensation products of this invention, the results are tabulated below.

amine. Then 54 ml formalin (37% $CH_2O$) to provide 0.658 mole formaldehyde is added at one time. As the reaction temperature increased extra heat is applied and nitrogen injection is started. Heating to and maintaining at 325°–350° F. for 2.25 hours was practiced. The dried liquid product (882.75 grams) is high molecular weight (1462 $\overline{Mn}$) Mannich condensation product in 256 grams of oil and has a viscosity of 3284.8 SSU at 210° F., a nitrogen content of 2.25%, an oxygen content of 1.57% and a specific gravity at 60° F. of 0.899. Those amounts of phenol, amine and aldehyde reactants provide the respective molar ratio of 1:0.5:1. This product is tested in a crankcase lubricant oil formulation in the Lincoln Sequence V Engine Test hereinafter described. That crankcase lubricant oil formulation contains:

| COMPONENT | VOLUME PERCENT |
|---|---|
| Base Oil | 94.8 |
| Product Example 9 | 4.0 |
| Zinc dialkyl dithiophosphate | 1.2 |

| | STIRRED OXIDATION TEST | | | | | | | | |
|---|---|---|---|---|---|---|---|---|---|
| Additive | Varnish | | | Naphtha Insolubles | | | Acidity | | |
| Example No. | 24 hr | 48 hr | 72 hr | 24 hr | 48 hr | 72 hr | 24 hr | 48 hr | 72 hr |
| 2 | 10 | 10 | 10 | 0 | 0 | 0.714 | 1.96 | 3.36 | 4.48 |
| 3 | 10 | 10 | 10 | 0 | 0 | 1.000 | 1.96 | 3.36 | 5.04 |
| 6 | 10 | 10 | 8 | 0 | 0 | 2.857 | 3.08 | 4.48 | 6.16 |

EXAMPLE 8

There are combined, heated and stirred at 200° F., 0.182 mole of polypropyl-substituted phenol (800 $\overline{Mn}$) and 0.031 mole tetraethylene pentamine. Then 0.182 mole formaldehyde is added as 14.7 ml. formalin (37% $CH_2O$) over a 45 minute period. Thereafter the temperature was increased to and held at 300° F. for four hours. Those amounts of phenol, amine and aldehyde reactants provided the respective molar ratio of 1:0.17:1. By-product water is removed. The dried product is all high molecular weight Mannich condensation product (1677 $\overline{Mn}$) containing 1.61% oxygen and having a viscosity of 7733 SSU at 210° F. Such a product is soluble in lubricating oil, e.g., SAE 5W, 10 and 30 weight oils, up to about 70 weight percent.

EXAMPLE 9

There are combined, heated and stirred at 200° F., 800 grams of SAE 5W oil solution containing 68 weight percent (0.658 mole) polypropyl-substituted phenol of 830 $\overline{Mn}$ and 62 ml (0.329 mole) tetraethylene pent- The sludge rating was 37.3 (50 is clean, no sludge), the varnish rating was 35.2 (50 is clean, no varnish) and oil ring plugging is 5%. Sludge and varnish ratings of 40 to 45 ranges can be achieved by increasing the concentrations of Example 9 product from 4 to 5 volume weight percent and also using 1.0 weight percent 300 total base number magnesium salt of an alkylated benzene sulfonic acid.

Example 9 is illustrative of the conventional one-step preparation of the high molecular weight Mannich condensation product prepared from high molecular weight alkyl-substituted phenol, polyamine and formaldehyde used in the respective molar ratio of 2:1:2.

EXAMPLE 10

The same reactants are used in the same amounts as in Example 9, but in the two-step condensation. 0.658 mole of the 827 $\overline{Mn}$ polypropyl phenol (68% in oil) and 0.329 mole of tetraethylene pentamine are combined, heated and stirred at 200° F. and to this stirred mixture 0.329 mole of formaldehyde is added. Then this product is heated at 300° F. to remove by-product water.

The the dry first condensation product cooled to 200° C. there is added 0.329 mole additional formaldehyde. This second condensation product is heated to 330° F. and nitrogen is injected until the product is dry. The dried product will have physical and chemical properties substantially the same as those shown for Example 8 product and will have substantially the same in-service use function as a dispersant-detergent additive agent for lubricating oils.

A high molecular weight Mannich condensation product can be prepared from melamine as the source of >NH containing reactant as illustrated by the following preparation.

EXAMPLE 11

There are combined, stirred and heated to 200° F., 200 grams of a solution of (83%) polypropyl-substituted phenol (0.186 mole) of 892 $\overline{Mn}$ in SAE 5W weight oil and 7.8 grams (0.062 mole) of melamine. Then 15 milliliters of formalin (37% $CH_2O$) to provide 0.186 mole formaldehyde is added and the mixture became milky white. The milky white appearance remained until the stirred mixture is heated to 470°–480° F. whereupon water vapors came off and water condensate appeared in an air cooled vapor take off condenser. The resulting product is heated at 370°–380° F. until dry. The ratio of substituted phenol, amine and formaldehyde reactants are in the respective molar ratio of 1:0.33:1. The dried product is an oil solution of the high molecular weight Mannich condensation product of melamine. A carbon black suspension test (conducted as hereinbefore described) provided a stable carbon black suspension for 64 hours.

EXAMPLE 12

An oil solution of high molecular weight Mannich condensation is prepared from 2500 grams of the oil solution (45.9%) of 1600 $\overline{Mn}$ polybutyl-substituted phenol (0.716 mole), 0.334 mole of tetraethylene pentamine and 1.20 mole of formaldehyde to provide the reactants in the respective molar ratio of 1:0.466:1.675. The solution of polybutyl-substituted phenol, tetraethylene pentamine and 350 grams of SAE 5W oil are combined, stirred and heated to 150° F. The addition of formaldehyde (as formalin) caused the temperature to increase to 180° F. Thereafter nitrogen is injected into the stirred solution and it is heated to 300° F. and held at that temperature for 3 hours while by-product water is thus driven off. The dry oil solution has a viscosity of 1175 SSU at 210° F. and a nitrogen content of 0.72%. The clarity of the solution is excellent before and after filtration. Spot Dispersancy Test values (test herein described) were 67.3 and 81.6 for 0.5 and 2.0 weight percent high molecular weight Mannich condensation product use, respectively.

EXAMPLE 13

An oil solution of 1654 Mn Mannich condensation product is prepared from 1000 grams 1280 Mn polypropyl phenol (0.64 mole) dissolved in SAE 5W oil as 77% solution, 0.64 mole formaldehyde (formalin), 0.32 mole tetraethylene pentamine and diluent SAE 5W oil are heated to 300° F. for 3.5 hours. A small amount of a polysilicon anti-foam agent is used to suppress foaming. The resulting solution of this high molecular weight Mannich product is bright although dark in color and has an oxygen content of 1.60% and 1.74% nitrogen.

The following examples illustrate the preparation of the preferred high molecular weight bis-Mannich products of respective reactant molar ratio 1.0:0.7–1.0:1–.5–2.1 using the before described two-staged condensation method of preparation.

EXAMPLE 14

To prepare N-mono-$C_{55}$ alkylbenzyl tetraethylene pentamine there is used an alkylphenol (mainly p-alkyl) of number average molecular weight ($\overline{Mn}$) of 890 (average of 55 carbons in alkyl groups) obtained by alkylating phenol with a polypropylene having about 55 carbon atoms. The alkylation product contains 80 percent by weight of said 890 $\overline{Mn}$ alkylphenol and 200 grams provides 0.18 mole of the 890 $\overline{Mn}$ alkylphenol. A mixture of 200 grams (0.18 mole) 80% of 890 $\overline{Mn}$ alkylphenol and 34 milliliters (0.18 mole) tetraethylenepentamine is stirred and heated to 210° F. and then 5.4 grams formalin (37% $CH_2O$) is added to provide 0.18 formaldehyde. The temperature of the reaction mixture increased to 300° F. Nitrogen at 1.5 (CFH) cubic feet per hour (measured at 77° F. and atmospheric pressure) is injected into the resulting reaction mixture at 320° to 340° F. for five hours. The resulting product is a light colored liquid. By analysis this product contains 4.46% nitrogen, 2.50% oxygen and has a 210° F. viscosity of 2466 SSU (Saybolt Seconds Universal). This product contains the N-mono-$C_{55}$ alkylphenol, formaldehyde and tetraethylene pentamine in the mole ratio of 1:1:1, i.e., equimolecular proportions of the three reactants.

The above product is stirred and cooled to 200° F. and 5.4 grams formalin (37% $CH_2O$) providing 0.18 mole formaldehyde is added. Thereafter this mixture is stirred and heated to 340° F., held at 340° F. while injecting nitrogen at 1.5 CFH for five hours. The resulting product is clear, dark and viscous. This product has a 210° F. viscosity of 14,515 SSU and by analysis has 3.14 weight percent oxygen and 4.14 weight percent nitrogen. The N-substituted amine product produced by the foregoing reaction is illustrated by substituting in structural formulae (I) and (II) $C_{55}$ alkyl for each R and $(HNC_2H_4)_4$ for each $(A-NH)_n$. This compound has a number average molecular weight of about 2196 and has 5.1 percent by weight nitrogen. The resulting product has 40 grams diluent, mainly residue nonreactive polypropylene from the alkylation, and thus the 4.14 percent nitrogen by weight of the product corresponds to about that of 0.09 mole of the foregoing substituted amine product with the 40 grams diluent.

An amount of the product of Example 14 containing 0.5 grams of the disubstituted amine shown is added to a measured volume of crankcase lubricant oil formulation which has been used in a Lincoln Sequence V Engine Test for 384 hours (twice the time of the standard test time). To the same volume of used crankcase oil from the same 394 hour Lincoln Sequence V Engine Test there is added 0.5 grams $N_1,N_5$-bis(polybutenyl-succinimide) of tetraethylene pentamine (Bis-Succinimide) whose polybutenyl group has a molecular weight of about 860. These two compositions are heated and stirred at 300° F. for 16 hours and an aliquot of each is transferred to blotting paper. A control is made at the same time by stirring and heating at 300° F. for 16 hours a third volume of used oil from the 394 hour Lincoln Sequence V Engine Test and depositing an aliquot on blotting paper. The remainder of each treated used crankcase oil (control-no addition agent)

is permitted to stand and the time is measured for the substantially complete separation of oil from sludge. The deposits on the blotting paper are measured to obtain the average diameter of the outer oil ring (Do) and the average diameter of the inner sludge ring (Ds). The ratio of Ds/Do is an indication of the detergent-dispersant property of the addition agent. These ratios and the sludge settling tests are shown in TABLE I.

TABLE I

| | Used Lincoln Sequence V Oil - 394 Hours | | |
|---|---|---|---|
| Test | Addition Agent | Sludge Settling | (× 100) Ratio Ds/Do |
| 1-Control | No | About one minute | About 60 |
| 2 | Example 14 (0.59) | 95 minutes | 89 |
| 3 | Bis Succinimide (0.59) | 19 minutes | 82.5 |

EXAMPLE 15

The process of Example 14 is repeated by heating and stirring 1000 grams (0.9 mole) of 1110 $\overline{M}n$ alkylphenol (alkyl group derived from polypropylene) and 170 milliliters (0.9 mole) tetraethylene pentamine (TEPA) to 200° F. and then adding formalin to provide 0.90 mole formaldehyde. Thereafter this mixture is heated to 300° F. with nitrogen injection at 1.0 CFH, during nitrogen injection the temperature increased to 350° F. and held at this temperature for 10–15 minutes and then dropped to 320° F. at the end of 2 hours nitrogen injection. The resulting product, a clear liquid, is diluted with 1200 grams SAE 5 oil (40 weight percent of the 1:1:1 reaction product. The oil diluted product is cooled to 200° F. and 0.9 mole formaldehyde is added with stirring. This mixture is heated to 340° F. and held at 340° F. while injecting nitrogen at 1.0 CFH for about 3 hours. The resulting product is filtered through celite at about 300° F. The resulting filtrate is a light colored, crystal clear product. The filtrate at 210° F. has a viscosity of 147.7 SSU and is found to contain 2.25 percent nitrogen and 1.66 percent oxygen, both by weight. The substituted amine product is a 1 mole alkylphenol:1 mole TEPA 2 moles formaldehyde compound.

EXAMPLE 16

The method of Example 14 is repeated using a 47% by weight solution of $\overline{M}n$ 900 alkylphenol (alkyl is from polypropylene) in SAE 5 oil to provide 0.85 mole of alkylphenol, 0.85 mole TEPA and two (69 ml.) portion of formalin (37% $CH_2O$) to provide 0.85 mole formaldehyde at each addition. The resulting filtered product is a dark, bright and clear liquid having viscosities of 352 SSU at 210° F. and 12,677 SSU at 100° F. By analysis this liquid product is found to contain on a weight basis 2.88% nitrogen, 1.2% oxygen, and 52% of the substituted amine product (like the structure depicted in Example 14) from the 1 mole Mn 900 alkylphenol:1 mole TEPA:2 moles formaldehyde reactant mole ratio.

EXAMPLE 17

There are combined 100 grams 2220 $\overline{M}n$ alkylphenol (0.045 mole), 100 grams SAE 5 oil and 0.045 mole TEPA. This mixture is stirred and heated to 187° F. and 0.045 mole for formaldehyde is added. This liquid mixture is stirred and heated to 320°–340° F. and nitrogen is injected at 1 CFH for 2 hours. Thereafter the liquid mixture is stirred and cooled to 200° F., a second addition of 0.045 mole formaldehyde is made and then the liquid mixture is stirred and heated again to 320°–340° F. with nitrogen injection at 1 CFH for about 3 hours. The resulting liquid is filtered at about 300° F. through celite. The filtrate is light in color, bright and clear liquid having a 210° F. viscosity of 2720 SSU. By analysis this product contains on a weight basis 0.85% nitrogen, 0.82% oxygen and about 40% of the 1 mole 2200 $\overline{M}n$ alkylphenol:1 mole TEPA:2 moles $CH_2O$ mole ratio substituted amine product.

EXAMPLE 18

There are combined, stirred and heated to 180° F., a solvent extracted SAE 5W oil solution containing 2.38 millimoles of alkylphenol obtained by alkylating phenol with a 70,000 $\overline{M}n$ polybutene (solution has a 100° F. viscosity of 38,880 SSU) and 2.38 millimoles TEPA. Then two additions of 2.38 millimoles formaldehyde are made at 140° F. and 160° F., respectively, with heating to 300–320° F. and 1 CFH nitrogen injection after each formaldehyde addition. By this method a very high molecular weight substituted amine product of 1 mole alkylphenol:1 mole TEPA:2 moles formaldehyde.

EXAMPLE 19

There are combined, stirred and heated to 160° F. 820 grams of 1800 $\overline{M}n$ alkylphenol (alkyl group derived from polybutene) providing 0.365 mole of said alkylphenol, 820 grams solvent extracted SAE 5W oil and 0.365 mole TEPA. Then 0.365 mole formaldehyde is added, the reaction mixture is stirred and heated to 320° F., held at 320° F. for 90 minutes and nitrogen is injected at 1.5 CFH at 260° F. for one hour. The liquid mixture is stirred and cooled to 180° F. and a second 0.365 mole formaldehyde addition is made, the resulting liquid reaction mixture is stirred and heated to 320° F., held at 320° F. for 90 minutes and nitrogen at 1 CFH is again injected at 260° F. This liquid is filtered through celite at about 260° F. The 210° F. viscosity of the filtrate is 687 SSU, and, by analysis, is found to contain 0.531% oxygen, 1.4% nitrogen, a total base number (TBN) of 30.61 and contain 42.5% of the 1 mole 1800 $\overline{M}n$ alkylphenol: 1 mole TEPA:2 moles formaldehyde mole ratio substituted amine.

EXAMPLE 20

There are combined, stirred and heated to 170° F. 700 grams solvent extracted SAE 5 oil, 0.284 moles TEPA and 966 grams of 2358 $\overline{M}n$ alkylphenol (alkyl group from polybutene) providing 0.284 mole of said alkylphenol. Then 0.284 mole of formaldehye is added, the mixture heated to 320°–340° F. and held at 320°–340° F. for 2 hours while injecting nitrogen at 2.0 CFH. An additional 0.284 mole of formaldehyde is added the liquid cooled to 180° F. and this liquid mixture is heated to 340° F., held at 340° F. for 2 hours while injecting nitrogen at 2 CFH. The liquid product is filtered. The filtrate has a 210° F. viscosity of 1191 SSU and is found to contain 1.13 percent nitrogen by weight. In this manner there is produced a solvent extracted SAE 5W oil solution of the 1 mole 2358 $\overline{M}n$ alkylphenol:1 mole TEPA:2 moles formaldehyde mole ratio substituted amine.

EXAMPLE 21

The process of Example 20 is repeated using 0.31 mole each of TEPA and 1937 $\overline{M}n$ polybutylphenol (polybutyl group has average of 131 carbons) as a 34 weight percent solution in SAE 5 oil. Two 0.31 mole $CH_2O$ portions are added at 180° F. with heating to 320° F. and nitrogen injection for 40 minutes after first addition and 150 minutes after second addition. The filtrate is a clear, bright liquid of light color having a 210° F. viscosity of 931 SSU, a 26.44 TBN and containing 1.2 percent nitrogen by weight. The product solute is of the mole ratio of reactants of 1 mole $C_{131}$ alkylphenol:1 mole TEPA:2 moles $CH_2O$.

EXAMPLE 22

In this preparation, bis-carbamide of TEPA, i.e. the compound

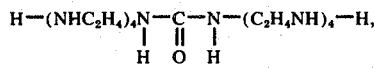

derived by reacting 2 moles TEPA with one mole urea to split out two moles ammonia is employed in place of TEPA. There is employed 0.031 mole of said bis-carbamide of TEPA, 0.031 mole of 1713 $\overline{M}n$ polybutylphenol dissolved in SAE 5W oil (143 grams of solution) and two 0.031 mole portions of $CH_2O$ each added at 180° F. with heating to 320° F. for 90 minutes and 1.5 CFH nitrogen injection after each addition. The resulting liquid product is filtered. The filtrate is a solution of the 1 mole — polybutylphenol:1 mole bis-carbamide of TEPA:2 moles $CH_2O$ substituted amine wherein the polybutyl substituent has an average of 115 carbons.

The use of bis-carbamide of polyalkylene polyamines, i.e. having the generic formula

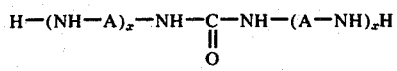

wherein $x$ and A are the integer and divalent alkylene hydrocarbon hereinbefore defined, in place of the polyalkylene polyamine is a convenient means for introducing nearly the same number of nitrogens into the product of 1 mole $C_{50+}$ alkylphenol:1 mole polyalkylene polyamine:2 moles $CH_2O$ by the use of a lower nitrogen lower molecular weight polyalkylene polyamine starting material in place of a higher molecular weight polyalkylene polyamine. In fact said bis-carbamides are useful replacements for TEPA. Also by the use of said bis-thiocarbamides wherein sulfur replaces oxygen in the generic formula hereinbefore shown, the sulfur provides extreme pressure lubricant properties to the detergent-dispersant oxidation inhibiting compounds of this invention.

EXAMPLE 23

As an example of such a sulfur-containing dispersant-detergent oxidation inhibiting compound of this invention, there are reacted 0.32 mole of thiourea and 0.64 mole of diethylene triamine to produce 0.32 mole bis-thiocarbamide of diethylene triamine:

under conditions splitting out two moles ammonia. Then 0.32 mole of this bis-thiocarbamide is combined with 1088 grams of 1836 $\overline{M}n$ $C_{124}$ alkyl-substituted phenol to provide 0.32 mole of $C_{124}$ alkylphenol. After stirring and heating this mixture to 140° F. there is added 0.32 mole formaldehyde, this mixture is heated to 340° F., held at 340° f. while injecting 2.2 CFH nitrogen for 75–80 minutes, cooled to 200° F., an additional 0.32 mole $CH_2O$ is added, and the resulting liquid is stirred and heated to 340° F. and nitrogen at 2.2 CFH is injected at 340° F. for 2 hours. The resulting mixture is filtered.

The detergency-dispersancy activity of the products of Examples 22 and 23 exceeds that of corresponding products prepared from TEPA or diethylene triamine (DETA) by more than the mere difference in nitrogen atom content might suggest.

EXAMPLE 24

Three preparations of 1 mole $C_{50+}$ alkylphenol:1 mole TEPA:2 moles formaldehyde products are carried out using 37 weight percent 1937 $\overline{M}n$ polybutylphenol, 37 weight percent 1713 $\overline{M}n$ polybutylphenol and 35 weight percent 1937 $\overline{M}n$ polybutylphenol each in SAE 5W oil as source of the $C_{50+}$ alkylphenol reactant. These preparations are hereinafter identified as 24A, 24B and 24C, respectively. The sequence of steps, conditions and amounts of reactants is set forth in TABLE II for these three preparations.

TABLE II

| Process Steps | | 24A | 24B | 24C |
|---|---|---|---|---|
| (1) | Combine, stir and heat | 0.35 mole each TEPA and alkylphenol | 0.54 mole each TEPA and alkylphenol | 0.45 mole each alkylphenol and TEPA |
| (2) | Add $CH_2O$ | 0.35 mole at 160° F. | 0.54 mole at 160° F. | 0.45 mole at 160° F. |
| (3) | Heat to 320° F. and hold with $N_2$ injection | 1.5 hour 1.5 CFH $N_2$ | 1.5 hour 1.5 CFH $N_2$ | 1.5 hour 1.5 CFH $N_2$ |
| (4) | Cool and add $CH_2O$ | 0.35 mole at 180° F. | 0.54 mole at 180° F. | 0.45 mole at 180° F. |
| (5) | Repeat Step (3) | 1.5 hour and 1.5 CFH $N_2$ | 1.5 hour and 1.5 CFH $N_2$ | 1.5 hour and 1.5 CFH $N_2$ |

TABLE II-continued

| Process Steps | 24A | 24B | 24C |
|---|---|---|---|
| (6) Filter | at 300° F. | at 300° F. | at 300° F. |

Small samples of 24A, 24B and 24C filtrates are taken and the remainder of 24A, 24B and 24C are combined and stirred. This mixture is hereinafter referred to as "Example 24 Composite Product" and is found to have a 210° F. viscosity of 780 SSU and a 29.88 TBN.

EXAMPLE 25

There are combined, stirred and heated to 140° F. 0.058 mole diethylene triamine and 306 grams of a 38% solution of 2000 $\overline{Mn}$ polybutylphenol (0.058 mole) in white oil. A first addition of 0.058 mole forcosity of 766 SSU and is found by analysis to have 1.25% nitrogen and a 31.4 TBN.

The screening detergent-dispersant test using crankcase drain oil from a Lincoln Sequence V engine test hereinbefore described is carried out with some of the products of the Examples of 13 through 27. There is shown in TABLE III the product used identified by Example number, the amount of reaction product in grams (not grams of solution produced) and the ratio of Ds (average diameter of sludge ring) and Do (average diameter of oil ring) × 100.

TABLE III

| Example | Control | 4 | 16 | 17 | 19 | 22 | 4 | 24[1] | 24[1] | 24A | 26 | 21 |
|---|---|---|---|---|---|---|---|---|---|---|---|---|
| Grams | None | 0.5 | 0.4 | 0.5 | 0.5 | 0.28 | 0.25 | 0.26 | 0.5 | 0.28 | 0.5 | 0.56 |
| Ds/Do × 100 | 60 | 92.5 | 87 | 89 | 97 | 77.5 | 71.5 | 79.4 | 90 | 84.3 | 88.4 | 93.8 |

[1] Composite of Example 24 maldehyde is made and the mixture is stirred and heated to 220° F. and held at 220° F. for 60 minutes. Thereafter the mixture is cooled to 200° F. and the second addition of 0.058 mole formaldehyde is made. This mixture is stirred and heated to 300° F. and held at that temperature for 2 hours. There is no evidence of unreacted formaldehyde or amine. The liquid product is filtered. The filtrate, a light and clear liquid has a 210° F. viscosity of 1531 SSU, a specific gravity of 0.8996 at 77° F. and from analysis is found to contain 0.67% nitrogen by weight.

By substituting 0.058 mole bis-carbamide derived from DETA in the foregoing reaction, a liquid product of 1.3 to 1.5% nitrogen by weight may be obtained.

EXAMPLE 26

There are combined, stirred and heated to 140° F. 0.477 mole DETA and 2500 grams of a 38% solution of 2000 $\overline{Mn}$ polybutylphenol (0.475 mole) in SAE 5W oil. A first addition of 0.475 mole formaldehyde is made and the mixture is stirred and heated to 220° F. The second addition of 0.475 mole formaldehyde is made 45 minutes later at 220° F., i.e. the reaction mixture is not cooled. The resulting liquid reaction mixture is then stirred and heated to 300° F., held at 300° F. for 2 hours and filtered at about 300° F. The filtrate, a light clear liquid has a 210° F. viscosity of 1418 SSU a specific gravity of 0.8967 at 77° F. and, by analysis, has 0.71% nitrogen by weight.

EXAMPLE 27

There are combined, stirred and heated to 140° F., a solution (2500 grams) containing 38% of 1713 $\overline{Mn}$ alkylphenol (0.482 mole) in SAE 5W oil and 0.482 TEPA. The first addition of 0.482 mole formaldehyde is made, the reaction mixture is stirred and heated to 300° F. with nitrogen injection at 1.5 CFH for 60 minutes, cooled to 160° F. for the second addition of 0.482 mole formaldehyde and then stirred and heated again to 300° F. with nitrogen injection at 1.5 CFH and reacted for 60 minutes. The liquid reaction mixture, SAE 5W oil solution of reaction product, has a 210° F. vis- The same test procedure conducted with 2:1:2 mole ratio of 830 $\overline{Mn}$ alkylphenol, 1140 $\overline{Mn}$ alkylphenol have Do/Ds × 100 ratios of 72 and 74, respectively at use of 0.5 grams. Those made from 2 moles of alkylphenol having 2 to 20 carbons in the alkyl substituent such as 1 mole nonylphenol:1 mole TEPA and 2 moles formaldehyde do not have a sufficiently oil soluble alkyl (R group) substituent on the ring of the hydroxy benzyl group of the di- and poly(hydroxyalkyl benzyl) amines to disperse sludge and hence show little or no improvement over the control.

EXAMPLE 28

There are combined, stirred and heated to 160° F., 2000 grams of SAE 5 oil solution of (45.9%) polybutyl-substituted phenol of 1600 Mn to provide 0.716 mole of that substituted phenol, 94 grams (0.495 mole) tetraethylene pentamine and 420 grams of SAE 5W oil. Then one drop of liquid silicon anti-foam agent and 100 milliliters of formalin (37% $CH_2O$) to provide 1.318 moles formaldehyde are added at one time to the hot stirred mixture. After the temperature increase from the reaction of the added formaldehyde has occurred, the temperature of the stirred solution of reaction product is increased to 300° F. and nitrogen is injected into stirred and heated solution. Nitrogen injection and stirring is continued while the solution is held at a temperature of about 310° F. (±10° F.) for two hours to drive off by-product water. Then the solution is filtered. The hot filtrate is bright, i.e., has a good clarity. The solution contains about 42% by weight of high molecular weight Mannich condensation product, a nitrogen content of 1.02% and a viscosity of 1002.5 SSU at 210° F. The reactants polybutyl-substituted phenol, amine and formaldehyde are used in the respective molar ratio of 1:0.69:1.835.

The product of the foregoing example, oil solution used with Lincoln Sequence V oil test (0.6% solute of Example 28), before described, gave a Ds/Do ratio of 91 which is indicative of super dispersant-detergent properties of the high molecular weight Mannich product.

ENGINE TESTS

The effectiveness of the substituted amine products of this invention as detergent-dispersant addition agent for lubricant oil compositions can be demonstrated by their use in such compositions as crankcase lubricants in actual engine tests such as the Lincoln Sequence V Engine Test, the Ford 289 Engine Test and the L-38 Engine Test aforementioned.

It will be noted that the hydroxyalkyl benzyl substituted amine products of this invention used in said tests unlike hydroxyalkyl benzyl substituted amines of the prior art are not used as their calcium, barium, magnesium or other alkaline earth metal or alkali metal salts.

The compounds of this invention can function as detergent-dispersant addition agents in lubricant oil compositions in the weight per cent range suitably of from 0.1 to 10%, desirably in the range of 0.2 to 8.0% and preferably in the range of 0.5 to 5%. However, lubricant oil solutions having 10 to 50% or more by weight of the novel hydroxyalkyl benzyl substituted polyalkylene amines of this invention including the bis(polyalkylene amine) carbamides and thiocarbamides are useful in the preparation of finished lubricant oil composition because they can be readily and conveniently combined with concentrates of other lubricant oil addition agents such as oil solutions of the alkaline earth metal sulfonates, e.g. normal and high based calcium and magnesium salts of petroleum sulfonic acids such as sour oil, mahagony acid and alkyl substituted benzene sulfonic acids having alkyl hydrocarbon groups of a carbon content of greater than 16 and more specifically of 30 to 20,000 carbon atoms alkyl hydrocarbon group size, oil solutions of zinc dialkyldithiophosphates and other concentrate solutions of lubricant addition agents all of which are used for their anti-wear, anti-corrosion, anti-foam, oxidation inhibition, oiliness, viscosity-index improving properties. For example, the oil solution concentrates having 10 to 50% by weight of the novel substituted amine products of this invention can be easily blend mixed with base oils and oil solution concentrates of the aforementioned addition agents having anti-wear, anti-corrosion, viscosity-index improving, anti-foam, etc. properties in transfer line blending, i.e. each concentrate and base oil are charged to a transfer line from sources of supply of each concentrate in the required proportions so that there flows from the transfer line a completely finished, fully formulated lubricant oil composition ready for packaging in quart, gallon, 5 quart, 30 gallon or 55 gallon containers or tank car and/or truck for delivery to the ultimate consumer. Such finished and fully formulated lubricant oil compositions are useful as crankcase lubricants for automobile, truck and railway gasoline and/or diesel engines.

The aforementioned Lincol Sequence V Engine Test, Ford 289 Engine Test and L-38 Engine Test are conducted in the following manner.

LINCOLN SEQUENCE V ENGINE TEST

Briefly, this test designed to evaluate dispersancy characteristics of formulated lubricant oils consists of using the oil to be tested as a lubricating oil in a V-8 Lincoln Engine under prescribed test conditions. Accordingly, five quarts of oil are placed in the crankcase and the engine is started and run in accordance with the four hour cycle:

|  | Phase 1 | Phase 2 | Phase 3 |
|---|---|---|---|
| Duration | 45 min. | 2 hr. | 75 min. |
| Speed, RPM | 500 | 2500 | 2500 |
| Load, Lbs. | No Load | —(105 HP) | —(105 HP) |
| Temperature, °F. |  |  |  |
| Water Out | 115–120 | 125–130 | 170–175 |
| Oil Sump | 120–125 | 175–180 | 205–210 |
| A/F | 9.5 ± 0.5 | 15.5 ± 0.5 | 15.5 ± 0.5 |

The four-hour cycle is reset a total of 48 times (192 hours running time). After each 16 hours of operation the engine is shut down for 8 hours. Two-ounce samples of oil are taken every 30 hours and the oil level is adjusted with fresh oil to a level of five quarts. Added oil is weighed. At the time of the test, the hot oil is drained, weighed and recorded. The engine is then disassembled and tested for deposits of varnish and sludge among other observable results as set out in the table below. Engine components are examined visually and rated on a scale of 1 to 10, 10 being a perfect reading indicating no sludge or varnish. A rating of 50 for total sludge and for total varnish is considered perfect; a rating of 60 per cent or lower is considered passing for screen clogging; and a rating of 50 per cent or lower is considered passing for ring plugging.

FORD-289 ENGINE TEST

The Ford 289 cubic inch displacement engine test, hereinafter designated as "F-289 Test," is conducted in the same manner as the Lincoln Test Sequence V except for the apparent difference in test engines. This F-289 Test is more severe with respect to both sludge and varnish formation and deposition. Also the F-289 Test is conducted with vapors from the crankcase being introduced into the engine fuel intake system by means of a positive crankcase ventilation system which, in part, results in the more severe sludge and varnish formation during test operation.

L-38 ENGINE TEST

The "L-38 Engine Test" is also known as CLR L-38 Engine Test and is designed to evaluate high temperature oxidation stablity of the formulated lubricant oil and such evaluation is based on piston varnish deposit and copper-lead bearing corrosion. In this test a single cylinder water cooled Labeco oil test engine is operated at 3150 rpm for 40 hours with the test oil formulation. The oil is maintained at 300° F. and cooling water is maintained at 195° F. Copper-lead connecting rod bearings are weighed before and after the 40 hour test. Bearing weight loss (BWL) of 50 milligrams or less is desired. After the 40 hour test the piston is visually evaluated and a varnish value is assigned by comparison to varnish deposit pictorial standards having assigned values of 1 to 10 for the color and extent of varnish deposit. In this varnish value scale of 1 to 10, the value 10 represents a clean and varnish free piston and the value 1 represents a substantially complete dark varnish coated piston. To qualify as a premium oil additive the varnish value should be 9.0 and above.

The following lubricant formulations in which all "%" of the addition agent indicated are by volume, are prepared for use in the foregoing engine tests. Products of this invention are identified by reference to the appropriate example of preparation and the volume % solution produced. The weight per cent of the solute product or dissolved is that of the "active ingredient", i.e. the dissolved substituted amine product, is shown under "weight %". Where used "Ca-300" and "Mg-300" designate the respective sulfonates dissolved as concentrates in SAE 5W oil with a total base number of 300 for the solution and other higher or lower numbers designate higher or lower solution total base members. The designation "ZOP" is used to identify a zinc dialkyldithiophosphate anti-wear-anti-corrosion addition agent whose alkyl groups are derived from the conjoint reaction of three different alcohols, two of which are primary alcohols such as $C_5$ and $C_{10}$ oxo-derived alcohols and the third is a secondary alcohol such as isopropyl or isobutyl alcohols, with dithiophosphoric acid and the total moles of the three alcohols is the stoichiometric amount required to obtain dialkyl dithiophosphoric acid for reaction with zinc or zinc oxide. Thus the ZOP is a statistical mixture of the zinc salts having the three aforementioned alcohol derived alkyl groups. Since the relative proportions of $C_3$ iso, $C_8$ primary and $C_{10}$ primary alcohols can be varied considerably to provide an oil-soluble zinc salt, their precise proportions need not be indicated. A "ZOP" product typical of that used is a concentrate zinc dialkyl dithiophosphate in SAE 5W oil having the following typical properties: Solution has 210° F. viscosity of 67 SSU, 5% Zn, 8% P and 16% S, all by weight.

TABLE IV

| Formulation No. | TEST OIL FORMULATIONS | | | | | | |
|---|---|---|---|---|---|---|---|
| | Example No. | Vol. | Wt. % | % ZOP | % Ca-300 | % Ma-300 | % Base Oil |
| I | 15 | 2.5 | 1.0 | 0.82 | 0 | 1.0 | 95.68 |
| II | 15 | 2.5 | 1.0 | 1.0 | 0 | 1.0 | 95.5 |
| III | 20 | 2.5 | 1.0 | 1.0 | 0 | 1.0 | 95.5 |
| IV | 20 | 5.0 | 2.0 | 1.0 | 1.0 | 0 | 93 |
| V | 24 | 4.0 | 1.6 | 1.0 | 1.0 | 0 | 94 |
| VI | 24 | 5.0 | 2.0 | 1.0 | 0 | 0 | 94 |
| VII | 27 | 5.0 | 2.0 | 0.62 | 0 | 1.0 | 93.38 |
| VIII | 13 | 4.4 | 2.0 | 1.20 | 0 | 0 | 94.33 |

The results of using above formulations in the Lincoln Sequence V Engine Test are presented in Table V.

TABLE V

| LINCOLN SEQUENCE V ENGINE TEST RESULTS | | | |
|---|---|---|---|
| Formulation No. | Sludge | Varnish | % Oil Ring Plugging |
| I | 37 | 38 | 21 |
| III | 46 | 42 | 0 |
| VII | 37.3 | 35.2 | 5 |

The results of the use of the indicated formulations in the Ford-289 Engine Test are given in Table VI.

TABLE VI

| FORD-289 ENGINE TEST RESULTS | | | |
|---|---|---|---|
| Formulation No. | Sludge | Varnish | % Oil Ring Plugging |
| IV | 50 | 40 | 0 |
| V | 45 | 37 | 0 |
| VI | 40 | 39 | 0 |

The results from the CLR L-38 Engine Test using the formulations indicated are given in Table VII.

TABLE VII

| CLR L-38 ENGINE TEST RESULTS | | |
|---|---|---|
| Formulation | Piston Varnish | Bearing Wt. Loss-Mg. |
| II | 9.5 | 32 |
| VII | 9.5 | 57 |

Lubricant oil formulations prepared from other of the products of this invention when used in the foregoing engine tests in the same or higher amounts of active ingredient will provide for the obtention of the same or superior results.

In general, the active ingredient product of this invention obtained as solute in light mineral oil have structural formulae as hereinbefore shown.

What is claimed is:

1. An oil-soluble high molecular weight Mannich product from the condensation of reactants:
   1. a high molecular weight alkyl-substituted phenol wherein said alkyl-substituent has an average number of carbon atoms of from 50 to 20,000 carbon atoms;
   2. an amine havng the formula:

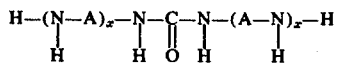

wherein $x$ is an integer from 1 to 10 and A is a divalent saturated hydrocarbon group having 2 to 3 carbon atoms; and 3. a formaldehyde affording reactant wherein the respective reactant molar ratio is 1.0:0.7–1.0:1-.5–2.1 prepared by combining reactants (1) and (2), adding thereto reactant (3) and heating the resulting mixture to a temperature in the range of 100°–350° F under conditions which remove by-product water.

2. The oil-soluble Mannich product of claim 1 wherein the alkyl-substituent of reactant (1) is polypropyl or polybutyl of 700 to 2500 $M_n$ and wherein the mixture of reactants (1) and (2) and two-thirds of reactant (3) is heated to a temperature in the range of 130–300° F until the resulting mixture is dehydrated and thereafter adding the remainder of reactant (3) and heating this mixture to a temperature of from 250–350° F until this mixture is dehydrated.

3. The oil-soluble Mannich product of claim 1 wherein reactant (1) is 1713 $\overline{M}_n$ polybutylphenol; in reactant (2) A is —$CH_2$—$CH_2$— and $x$ is 4; reactant (3) is formaldehyde; and the respective reactant molar ratio is 1.0:1.0:2.0 prepared by combining reactants (1) and (2), adding thereto one-half of reactant (3) at 180° F and heating the mixture to a temperature of 320° F under conditions which remove by-product water, cooling the water-free reaction mixture to a temperature of 180° F, adding thereto the remaining one-half of reactant (3), and heating the resulting mixture to a temperature of 320° F under conditions which remove by-product water.

* * * * *

UNITED STATES PATENT OFFICE
CERTIFICATE OF CORRECTION

Patent No. 3,985,802    Dated October 12, 1976

Inventor(s) Edmund J. Piasek and Robert E. Karll    Page 1 of 2

It is certified that error appears in the above-identified patent and that said Letters Patent are hereby corrected as shown below:

In Abstract, line 5 "(Mn)" should be --($\overline{Mn}$)--.

Col. 2, line 58, "2,363,124" should be --2,363,134--.

Col. 2, line 58 "3,459,112" should be -- 2,459,112 --.

Col. 4, line 30 replace "of ashless" with --as ashless--.

Col. 4, line 58 replace "depost" with --deposit--.

Col. 6, line 56, quotes are reversed before "tail-to.

Col. 7, line 45 "Mn" should be --$\overline{Mn}$--.

Col. 9, line 26, "Mn" should be --$\overline{Mn}$--.

Col. 15, line 58, "Mn" should be --$\overline{Mn}$--.

Col. 15, line 59 "Mn" should be --$\overline{Mn}$--.
Col. 17, line 49 "portion" should be --portions--.

Col. 17, line 57 "Mn" should be --$\overline{Mn}$--.

Col 18, line 25 "witha" should be --with a --.

Col. 20, line 34 "340°f." should be --340°F --.

Col. 22, line 42 "Mn" should be --$\overline{Mn}$--.

Col. 23, line 25 "composition" should be --compositions--.

Col. 23, line 57 "Lincol" should be --Lincoln--.

UNITED STATES PATENT OFFICE
CERTIFICATE OF CORRECTION

Patent No. 3,985,802      Dated October 12, 1976

Inventor(s) Edmund J. Piasek and Robert E. Karll    Page 2 of 2

It is certified that error appears in the above-identified patent and that said Letters Patent are hereby corrected as shown below:

Col. 24, line 43 should read "CLR L-38 Engine Test"

Col. 25, line 7 "members" should be --numbers--.

Col. 25, line 33-34, under Example "Vol" should be --Vol.%--.

Col. 25, line 31, "%Ma-" should read --%Mg--.

Col. 26, line 44 "Mn" should be --$\overline{Mn}$--.

Signed and Sealed this

Thirty-first Day of May 1977

[SEAL]

Attest:

RUTH C. MASON  
*Attesting Officer*

C. MARSHALL DANN  
*Commissioner of Patents and Trademarks*